United States Patent [19]

Loen

[11] Patent Number: 5,109,157
[45] Date of Patent: Apr. 28, 1992

[54] ION MOBILITY DETECTOR

[76] Inventor: Andrew E. Loen, 1851 Thomas Argue Rd., R.R. #3, Carp, Ontario, Canada, K0A 1L0

[21] Appl. No.: 672,825

[22] Filed: Mar. 21, 1991

[51] Int. Cl.⁵ .............................................. H01J 49/40
[52] U.S. Cl. .................................... 250/287; 250/281
[58] Field of Search ............... 250/287, 286, 281, 282; 422/98

[56] References Cited

U.S. PATENT DOCUMENTS

| | | | |
|---|---|---|---|
| 3,616,182 | 12/1971 | Cohen | 250/41.9 TF |
| 3,626,178 | 12/1971 | Cohen | 250/41.9 TF |
| 3,626,179 | 12/1971 | Cohen | 250/41.9 TF |
| 3,626,180 | 12/1971 | Carroll et al. | 250/41.9 TF |
| 3,626,181 | 12/1971 | Wernlund | 250/41.9 TF |
| 3,697,748 | 10/1972 | Cohen | 250/41.9 TF |
| 3,845,301 | 10/1974 | Wernlund et al. | 250/28 P |
| 4,238,678 | 12/1980 | Castleman et al. | 250/287 |
| 4,261,698 | 4/1981 | Carr et al. | 23/232 |
| 4,311,669 | 1/1982 | Spangler | 422/98 |
| 4,378,499 | 3/1983 | Spangler et al. | 250/287 |
| 4,390,784 | 6/1983 | Browning et al. | 250/287 |
| 4,445,038 | 4/1984 | Spangler et al. | 250/387 |
| 4,551,624 | 11/1985 | Spangler et al. | 250/287 |
| 4,633,083 | 12/1986 | Knorr et al. | 250/282 |
| 4,712,008 | 12/1987 | Vora et al. | 250/287 |
| 4,777,363 | 10/1988 | Eiceman et al. | 250/286 |
| 4,797,554 | 1/1989 | Blanchard et al. | 250/287 |
| 4,839,143 | 6/1989 | Vora et al. | 422/98 |
| 4,855,595 | 8/1989 | Blanchard | 250/287 |

FOREIGN PATENT DOCUMENTS 2002574 7/1978 United Kingdom .

Primary Examiner—Jack I. Berman
Attorney, Agent, or Firm—Hoffman, Wasson & Citler

[57] ABSTRACT

An ion mobility detector comprising a one piece dielectric tube with conductive bands as field elements for accelerating ions formed in a reactor region of the tube and passed to a drift region of the tube under control of a gate separating the reactor region from the drift region and thence to an electrometer plate. A first d.c. voltage source provides operating voltages to the conductive bands while a separate d.c. voltage source provides operating voltages to the gate. The detector includes circuitry for varying the potential of the gate to ensure correct focusing of ions within the cell. The circuitry includes an arrangement for altering the potential of the gate. The arrangement can be automatically controlled as a function of the output of an amplifier connected to the electrometer plate.

13 Claims, 4 Drawing Sheets

GATE = 1900v

ION MOBILITY DETECTOR

BACKGROUND OF THE INVENTION

This invention relates to an ion mobility detector in which ions formed in a reactor region of a tubular cell are passed to a drift region of the tube under control of a gate separating the reactor region from the drift region and thence to an electrometer plate.

Ion mobility detectors are known in the prior art. Briefly stated, they comprise tubular structures having a reactor region, a drift region and an electrometer plate. A gas to be analyzed, together with a carrier gas such as air, is introduced into the reactor region where it is ionized, e.g. by a radioactive material contained therein. Voltages applied to a gate between the reactor region and the drift region allow samples of the ions to enter the drift region where they are accelerated by an electric drift field. The ion samples reach terminal velocity dependent on their mass and may be sorted depending on the time they take to travel from the gate to the electrometer plate at the end of the drift region.

The drift field may be produced in various ways, e.g. by ring-like electrodes on a surface (interior or exterior) of an insulating tube to which voltages are applied. Resistors connect adjacent electrodes and a high voltage is applied between the end electrodes. The resistors create an electric field gradient along the tube. Instead of discrete resistors, some prior art detectors use a continuous film of resistive material. See, for example, U.S. PAt. No. 4,390,784 of Browning, et al, issued Jun. 28, 1983.

In an alternative construction the drift tube is formed by alternating rings of metal and insulating material.

The operation of a drift tube is explained in more detail in U.S. Pat. No. 3,621,240 of Cohen, et al, issued Nov. 16, 1971.

The following U.S. patents relate to one piece cell designs and sampling techniques:

| | |
|---|---|
| 4,390,784 | Browning, et al |
| 4,712,008 | Vora et al |
| 4,777,363 | Eiceman et al |

As a result of extensive research it has been determined that there are a number of key factors to be taken into consideration in connection with an ion mobility detector to ensure that ions in the cell are sufficiently focused and that space charge problems are not encountered. These key factors are:

1. a distinct trasition from the smaller diameter tube portion (reaction region) to the larger diameter tube portion (drift region), with the elbow where the two tube portions meet coated in a conducting layer to act as a second repeller plate,
2. the placement of the Ni-63 radioactive ionizing source on the interior of the tube so that it is aligned with a clearly defined conducting band on a surface of the tube,
3. a well defined internal repeller plate,
4. care in not having any portion of the cell wall, or the cements used therein, protruding into the cell volume, and
5. an adjustable gate potential to allow the formation concave field lines which properly focus the ions.

Some of these factors are known in the prior art. Examples for some of the above points are the following U.S. patents:

| | |
|---|---|
| 1. | Wernlund et al, #3845301, Spangler et al, #4551624 Spangler et al, #4378499, and Vora et al, #4839143 |
| 2. | Wernlund et al, #3845301, and Spangler et al, #4378499 |
| 3. | Wernlund et al, #3845301, and Spangler et al, #4311669 |
| 4. | Ordinary knowledge in the prior art. |

The adjustable gate potential, however, is not demonstrated in any of the prior art.

SUMMARY OF THE INVENTION

The prior art of IMS used a single resistance ladder to supply the voltages that are required along the length of a cell. The potential of the gate was determined by the physical position of the gate along the length of the cell. The same can be said of the newer designs of cells that use a solid dielectric tube with a film resistor disposed on the inside surface; the potential of the gate was determined by the potential that occurred by default at the joint of the reaction region and the drift tube. It has been determined that this is not the optimum potential for the gate. Computer modelling of the field lines within the cell, combined with experimental avidence, has shown that the optimum potential for the gate is typically lower than the expected value.

Computer modelling (using Simion) permited viewing electric field lines in three dimensions. A model of the conductive bands that are used in an IMS cell was used to generate maps of the field lines. The potential of the gate was then varied and the focusing efficiency for each case was determined. This yielded the optimum theoretical potential for the gate.

The computer modelling was followed by experimental work. A cell was built that used a second external resistance ladder to determine the potential of the gate. The gate was held fully open and the full ion current being focused onto the electrometer disk was monitored with a picoammeter. The full ion current as a function of the gate potential was measured and plotted, and the optimum potential for the gate was determined.

It is noted that this work was done using an IMS cell that is characterized by external conductive bands on a dielectric tube. With this design of cell it is particularly important that the gate potential be optimized correctly and, while not so critical for IMS cells having internal conductive field elements, it is believed that they would produce a stronger signal if the above gate potential optimization was performed.

It might not be clear from the prior art what exactly is meant by the adjustment of the gate potential. In the normal operation of the IMS cell the two sets of gate wires forming two sides of the gate are each held at a particular potential, with a difference of approximately 50 V between the two sides of the gate; i.e. one side of the gate would typically be 1950 V while the other side would be maintained at 2000 V. When the gate drive circuit would open the gate, the two sides would be shorted together; i.e. they would both be at 2000 V. In the present invention, the gate is still maintained with approximately 50 V between the opposite sides; however the high voltage point is varied and this high voltage point is referred to herein as "the open gate potential", "the open gate voltage" or, for brevity, "the gate potential". The gate potential is typically adjusted between 1700 V and 2250 V.

It was also found that the optimum potential of the gate varied with the temperature of the cell. As the IMS cell was heated from ambient temperature to 350° C., the potential of the gate had to be adjusted to maintain the correct focusing of the ions within the cell. The reason for this is not fully understood.

DESCRIPTION OF THE PREFERRED EMBODIMENTS

Figure 1:
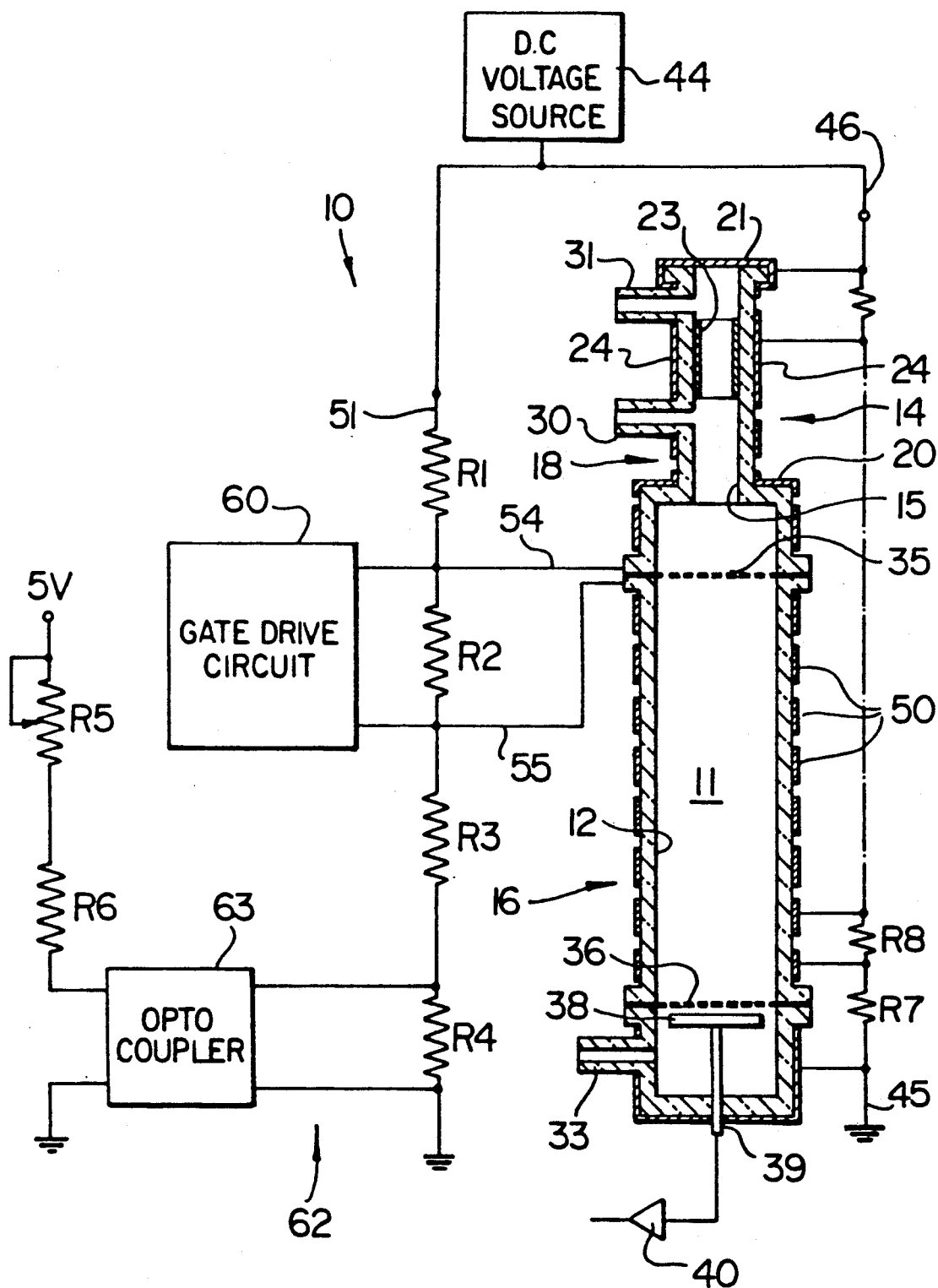
FIG. 1 is a diagram of an ion mobility detector in accordance with the invention.

Referring to FIG. 1, an ion mobility detector according to the invention is generally indicated at 10. The cell portion 11 of the detector comprises a tube 12 of dielectric material such as glass or ceramic defining a drift region 16 and a tube 15 defining a reactor region 14. There is a sharp transition from the smaller diameter tube 15 to the larger diameter tube 12 and the outer surface of the elbow in the transition region 18 is provided with a conductive layer 20 which acts as a second repeller plate, the first repeller plate, indicated at 21, being at the outer end of the tube 15.

The interior of tube 15 is provided with a band of radioactive material 23, such as Ni-63, which is aligned with a conductive band 24 on the exterior of tube 15.

Tubes 12 and 15 may be fused or cemented together. Care should be taken to ensure that portions of the cell wall or cements used therein do not protrude into the cell volume.

The cell is provided with a sample inlet 30, an exhaust 31, a drift gas inlet 33, a gate 35, an aperture grid 36 and an electrometer plate 38 mounted on a conductive support member 39 which extends through the outer end of tube 12. The support member 39 is adapted to be connected to a picoammeter (not shown) or to an amplifier 40 for providing an output signal proportional to current (ions) received by plate 38.

The tubes 12 and 15 have external conductive bands such as indicated at 24 and 50 to which different d.c. voltages are applied from a d.c. voltage source 44 via a resistor chain 45. To simplify the drawing, resistor chain 45 is shown with only a few resistors, but in practice there would be several more resistors depending on the number of conductive bands on tubes 12 and 15. Taps at the ends of resistors R7 and R8 are shown, by way of example, connected to some of the conductive bands 50. The other bands 50, and the bands 24, are connected to other taps on the resistor chain 45 to form electric fields within the cell to accelerate ions toward the electrometer plate 38. One end of resistor chain 45 is grounded as shown while the other end 46 is connected to a high voltage d.c. source 44, e.g. a 3000 volt d.c. source.

The basic operation of the ion mobility detector involves introducing into the cell 11, via sample inlet 30, a sample gas together with a carrier gas such as air. The sample enters the reactor region 14 where it is ionized by the band of radioactive material 23. The resulting ions are repelled towards the drift region 11 by repeller electrode 21 to which a high voltage is applied from the top end of the resistor chain 45. The ions are accelerated through the reactor region by electric fields developed by voltages applied from resistor chain 45 to coonductive bands 24 on the outer surface of tube 15. Once ions have entered the tube 12 they are further urged into it by second repeller 20.

Entry of ions from the reactor region 14 to the drift region 16 is controlled by the gate or grid 35 which comprises two sets of parallel wires. The two sets of gate wires have different voltages applied to them when the gate is closed via leads 54 and 55 connected across a resistor R2 in a second resistor chain 51. Resistor chain 51 is shown connected d.c. voltage source, e.g. 44 but it could be connected to a separate d.c. voltage source, e.g. 2200 V. The values of resistors R1 to R4 are selected to provide proper gate potentials depending on the voltage of the d.c. source to which resistor chain 51 is connected. The voltage difference between the two sets of wires when the gate is closed may be, for example, 50 volts with the wires connected to lead 54 being at a higher voltage than the wires connected to lead 55. For example the first set of wires, connected to lead 54, would typically be at 2000 V while the second set of wires connected to lad 55, would be at 1950 V.

To open the gate, the gate drive circuit 60 shorts the two sets of wires together, at which time they are both at 2000 V, allowing ions to pass from the reactor region to the drift region. Since the two sets of gate wires are at the same potential, it is referred to as "the open gate potential", it being seen that this is always the potential of the gate wires connected to higher potential, i.e. to lead 54 in FIG. 1.

As mentioned above, prior art IMS detectors used a single resistance ladder to supply voltages required for the different electrodes along the length of the cell. The open gate potential is thus determined by the physical position of the gate along the length of the cell or at least its points of connection to the resistance ladder. In other words, the open gate potential is predetermined for a particular detector. However, I have determined that this is not necessarily the optimum potential for the gate. Computer modelling of the field lines within the cell, combined with experimental evidence, has shown that the optimum potential for the gate is typically lower than the expected value.

Computer modelling, using a program called "SIMION" (trade mark), permitted viewing electric field lines in three dimensions. A model of the conductive bands used in a cell of the type shown in FIG. 1 was used to generate maps of the field lines. The potential of the gate was then varied and the focusing efficiency for each case was determined. This yielded the optimum theoretical potential for the gate.

Figure 2:
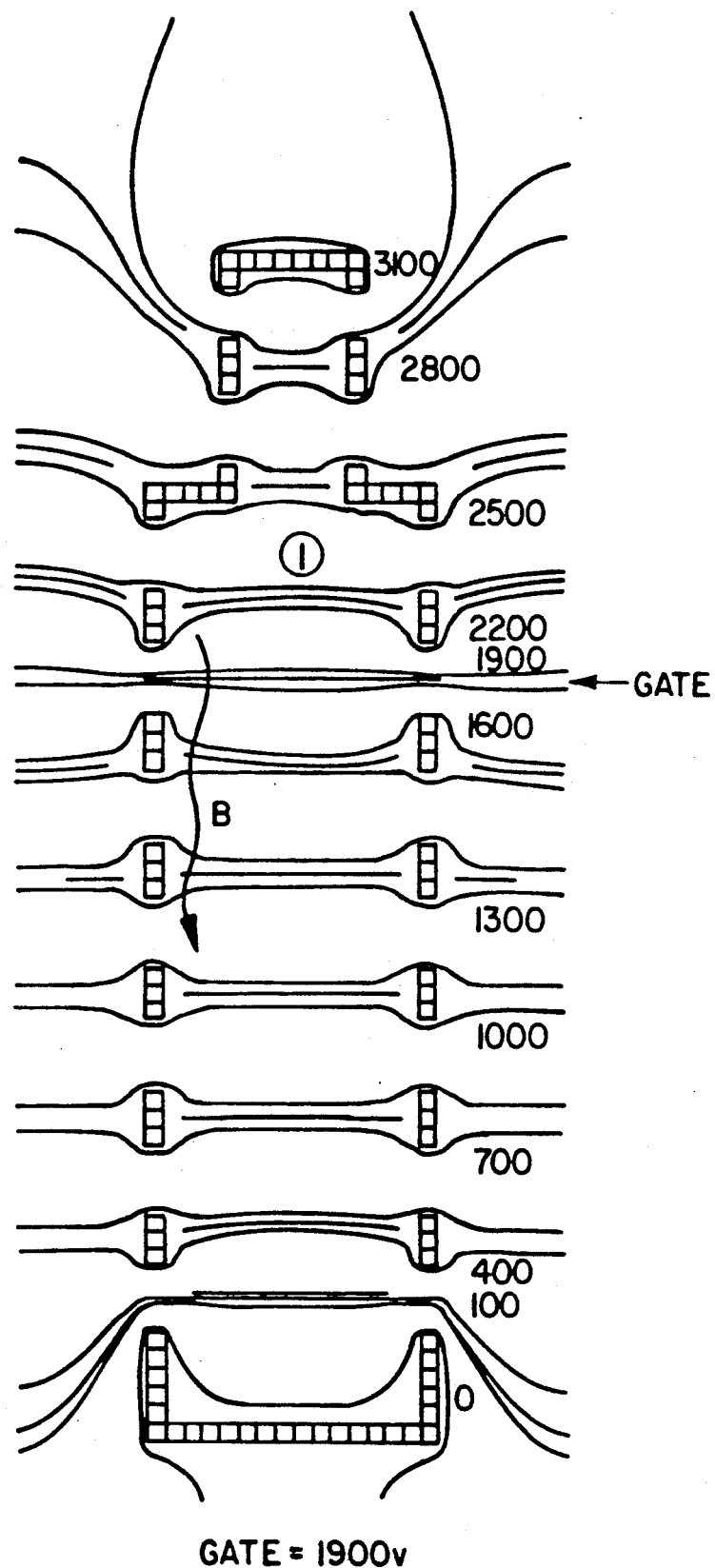
FIG. 2 is a map of the equipotential surfaces in a typical prior art ion mobility detector.

FIG. 2 is a map of the equipotential surfaces in a typical prior art IMS cell. The gate potential assumes a default value that occurs at the junction of the reaction and drift regions of the cell where the gate is attached. Ions at atmospheric pressure in the IMS cell are accelerated perpendicular to these equipotential surfaces. Note that the equipotential surfaces in region 1 of FIG. 2 are approximately parallel. The ions which traverse this region are not focused very strongly.

Referring again to FIG. 1, the detector according to the invention includes an external gate drive circuit generally indicated at 62. The circuit 62 includes a potentiometer R5 which is adjustable to vary the driving current and hence the brightness, of an LED in opto-coupler 63. A photoconductive cell in opto-coupler 63 changes its resistance from 1000 Meg ohm to 1 kilo ohm depending upon the brightness of the LED. This variable resistance of the photoconductive cell is in parallel with a portion of the resistor chain 51, here shown as resistor R4. When the photoconductive cell is at 1000 Meg ohm, the gate potential is held at a first voltage, e.g. 2250 V. When the photoconductive cell is at 1 kilo ohm, the resistor R5 is effectively shorted, and the gate potential drops to a second voltage, e.g. 1500 V.

Figure 3:
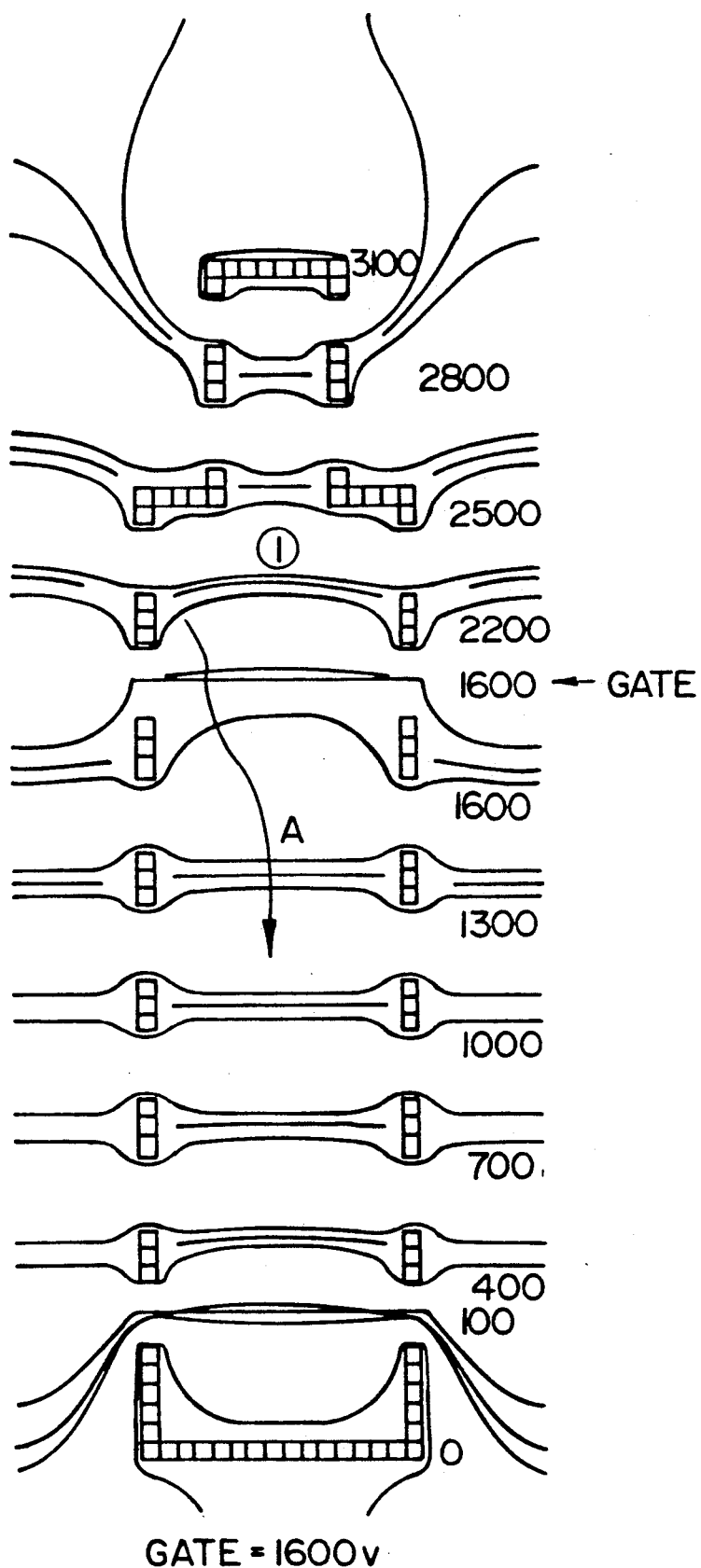
FIG. 3 is a map of the equipotential surfaces in an ion mobility sensor according to the invention with the gate held at the optimum potential.

FIG. 3 is a map of the equipotential surfaces in an IMS cell according to the invention, with the gate held at the optimum potential. Note that the equipotential surfaces in region 1 are strongly concave in shape. This provides proper focusing of the ions in the cell providing a higher concentration of them on the axis of the cell immediately in front of the gate in the drift region.

The non-optimum ion focusing that is found in all prior art IMS cells (due to the fixed gate potential) has two serious deficiencies. The first is that the signal strength is reduced, due to the loss of ions that are not sufficiently focused and hence impinge on the walls of the cell. The second is that the poorly focused ions which travel off axis down the drift tube cause peak broadening in the ion mobility spectra. This is because ions that travel off axis in the drift tube are subject to an oscillating field which results in a longer path of travel and therefore longer transit time than for those ions which travel in the center of the tube. See path A in FIG. 3 vs p path B in FIG. 2.

Figure 4:
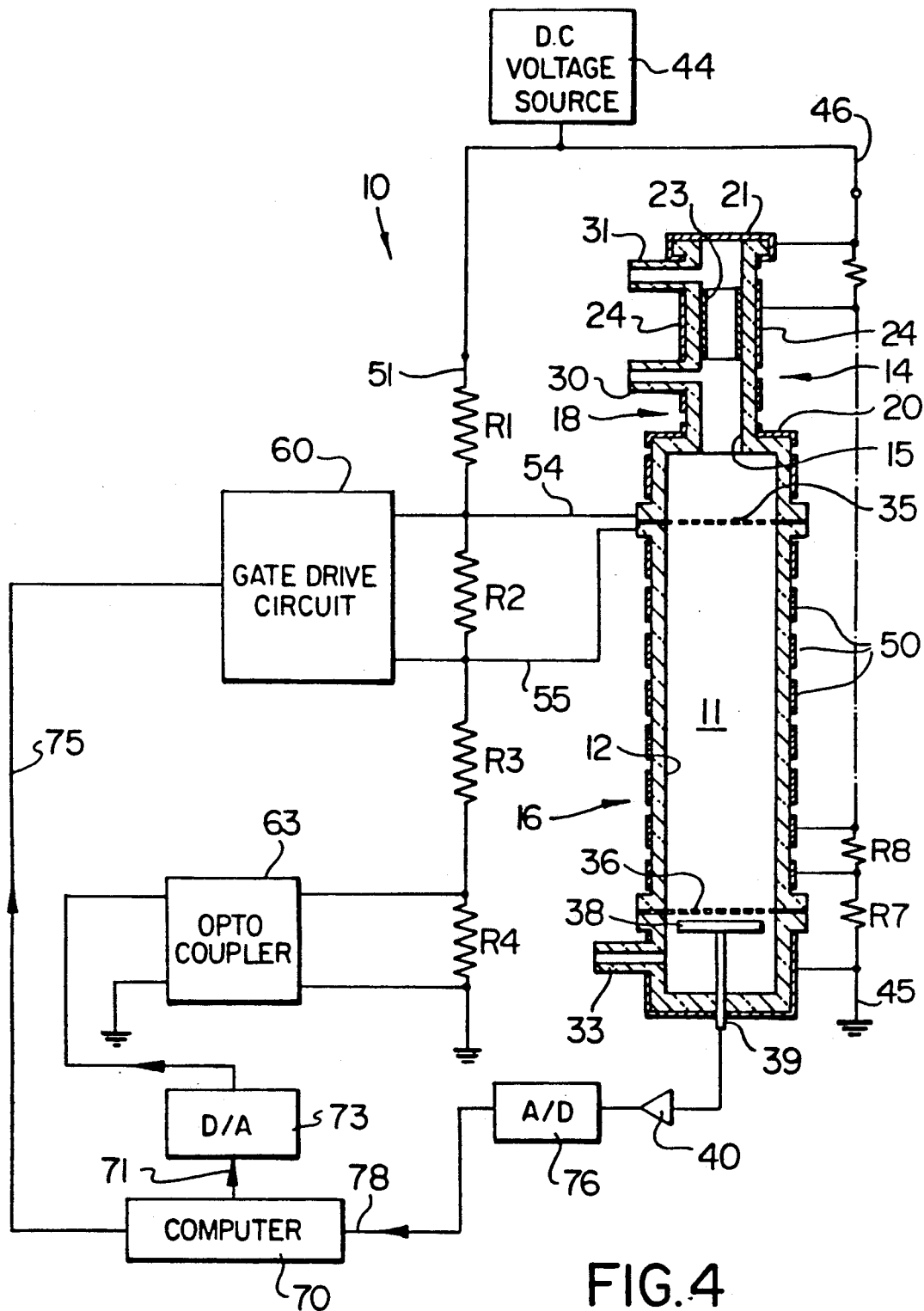
FIG. 4 illustrates a modification of the circuitry shown in FIG. 1 whereby the gate potential can be automatically set to an optimum value.

FIG. 4 illustrates a modification of the circuitry of FIG. 1 which enables the potential of the gate to be automatically set to the optimum value. In FIG. 4, the LED of the opto-coupler 63 is controlled by an output 71 of a computer 70 after conversion, if necessary, to an analog signal by A/D converter 73. The computer 70 also controls, via an output 75, the gate drive circuit 60. Furthermore, the computer 70 monitors the output of the ion mobility detector, which output at 39 is amplified at 40, converted to a digital signal by A/D converter 76 and fed to input 78 of computer 70. The computer 70 temporarily holds the gate fully open via its output 75 to gate drive circuit 60 and then varies the gate potential via its output 71 while monitoring the output of the detector. Once the computer senses that the optimum gate potential (highest detector output current) has been found, the computer releases the gate drive circuit so that it can resume normal operation. Optimization of the gate potential can be determined prior to a measurement operation by the ion mobility detector. Because the gate potential is adjusted in accordance with the measured output current of the cell, changes in operation of the cell due to temperature changes are automatically compensated for.

While FIGS. 1 and 4 show preferred embodiments of the invention various modifications will be evident to those skilled in the art. For example the field elements could be on the interior surface of the wall of the cell instead of on the exterior. Also, a separate, variable d.c. voltage source could be used for the gate potential with the source directly controllable by the computer. The computer can be a microcomputer.

What is claimed is:

1. An ion mobility detector operable at atmospheric pressure comprising a tube of suitable dielectric material having an inlet for receiving a sample gas and a carrier gas, a reactor region for generating ions from the sample gas, a gate separating said reactor region from a drift region, and an electrometer plate for collecting ions that traverse said drift region, said reactor region and said drift region being provided with conductive field elements for accelerating said ions, said field elements being connectable to a first d.c. voltage means and said gate being connectable to a second d.c. voltage means having an adjustable output, said detector including means to vary said output of said second d.c. voltage means when said gate is open to adjust focusing of ions in said detector to ensure optimum operation of said detector.

2. A detector as claimed in claim 1 wherein said first d.c. voltage means includes a d.c. voltage source connected across a first voltage divider comprising a first chain of resistors, voltage taps between adjacent resistors being connected to said field elements.

3. A detector as claimed in claim 2 wherein said second d.c. voltage means comprises a d.c. voltage source connected across a second voltage divider, voltage taps on said second voltage divider being connected to said gate.

4. A detector as claimed in claim 3 wherein said means to vary said output of said second d.c. voltage means comprises means to shunt variable amounts of current from said second voltage divider whereby to vary the voltage across said second voltage divider.

5. A detector as claimed in claim 4 wherein said means to shunt current comprises an opto-coupler having an LED input and photoconductive cell output, said LED input being connected to means for varying current through said LED and said output being connected across said portion of said second voltage divider.

6. A detector as claimed in claim 5 including means for monitoring current at said electrometer plate while said gate is open and current through said LED is varied to thereby vary the voltage on the open gate.

7. A detector as claimed in claim 6 including computer means for adjusting current through said LED and for monitoring current flow at said electrometer plate.

8. A detector as claimed in claim 5 including a computer for monitoring current at said plate, for controlling opening and closing of said gate and for controlling variations in said open gate voltage, said computer varying said open gate voltage while holding the gate open and monitoring the current at said plate so as to maximize said current.

9. A detector as claimed in claim 8 wherein said computer varies said open gate voltage by varying current through said LED input.

10. A detector as claimed in claim 9 wherein said computer opens and closes said gate by controlling a gate drive circuit connected to said gate.

11. A detector as claimed in claim 10 wherein said field elements are on a surface of said tube.

12. A detector as claimed in claim 11 wherein said surface is an external surface of said tube.

13. A detector as claimed in claim 12 wherein said first and second d.c. voltage means comprise first and second d.c. voltage sources.

* * * * *